United States Patent [19]
Milburn et al.

[11] Patent Number: 6,103,878
[45] Date of Patent: Aug. 15, 2000

[54] ANTIBODY TO CARBOXY-TERMINUS OF HUMAN HERPESVIRUS 6 IMMEDIATE EARLY PROTEIN

[75] Inventors: Gary L. Milburn, Rogers, Ark.; Robert E. Novy, Jr., Verona; Robert C. Mierendorf, Jr., Madison, both of Wis.

[73] Assignee: Pel-Freez Rabbit Meat, Inc., Rogers, Ark.

[21] Appl. No.: 09/084,574

[22] Filed: May 26, 1998

Related U.S. Application Data

[62] Division of application No. 08/683,060, Jul. 16, 1996, Pat. No. 5,756,302.
[51] Int. Cl.[7] .......................... A61K 39/42; C07K 14/03; C07K 16/08
[52] U.S. Cl. ..................................... 530/387.9; 424/185.1; 424/186.1; 424/229.1; 435/5; 435/7.1; 435/7.92; 530/387.1; 530/388.3; 530/389.4; 536/23.72
[58] Field of Search .............................. 424/185.1, 186.1, 424/229.1; 435/7.1, 7.92, 5; 530/387.1, 387.9, 388.3, 389.4; 536/23.72

[56] References Cited

PUBLICATIONS

Chiou et al. J. Virol. vol. 67, No. 10, Oct. 1993, pp. 6201–6214.
Carrigan, D.R., "Human Herpesvirus–6 and Bone Marrow Transplantation", *Human Herpesvirus–6*, Ablashi/Krueger/Salahuddin Editors, Chapter 21:281–301, (1992).
Carrigan et al., "Human Herpesvirus 6 (HHV–6) Isolation from Bone Marrow: HHV–6–Associated Bone Marrow Suppression in Bone Marrow Transplant Patients", *Blood* 84:3307–3310 (1994).
Chou et al., "Analysis of Interstrain Variation in a Putatuve Immediate–Early Region of Human Herpesvirus 6 DNA and Definition of Variant–Specific Sequences", *Virology* 198:370–376 (1994).
Cone et al., "Human Herpesvirus 6 DNA in Peripheral Blood Cells and Saliva from Immunocompetent Individuals", *J. Clinical Microbiology* 31:1262–1267 (1993).
Cone et al., "Human Herpesvirus 6 in Lung Tissue from Patients with Pneumonitis After Bone Marrow Transplantation", *The New England J. Medicine* 329:156–161 (1993).
Dewhurst et al., "Human Herpesvirus 6 (HHV–6) Variant B Accounts for the Majority of Symptomatic Primary HHV–6 Infections in a Population of U.S. Infants", *J. Clinical Microbiology* 31:416–418 (1993).
Drobyski et al., "Human Herpesvirus–6 (HHV–6) Infection in Allogeneic Bone Marrow Transplant Recipients: Evidence of a Marrow–Suppressive Role for HHV–6 In Vivo", *J. Infectious Diseases* 167:735–739 (1993).
Drobyski et al., "Prevalence of Human Herpesvirus 6 Variant A and B Infection in bone Marrow Transplant Recipients as Determined by Polymerase Chain Reaction and Sequence-Specific Oligonucleotide Probe Hybridization", *J. Clinical Microbiology* 31:1515–1520 (1993).
Gleaves et al., "Rapid Detection of Cytomegalovirus in MRC–5 Cells Inoculated with Urine Specimens by Using Low–Speed Centrifugation and Monoclonal Antibody to an Early Antigen", *J. Of Clinical Microbiology* 19:917–919 (1984).
Gleaves et al., "Comparison of Standard Tube and Shell Vial Cell Culture Techniques for the Detection of Cytomegalovirus in Clinical Specimens", *J. Clinical Microbiology* 21:217–221 (1985).
Jacobs et al., "Characteristics of a Human Diploid Cell Designated MRC–5", *Nature* 227:168–170 (1970).
Knox et al., "Disseminated Active HHV–6 Infections in Patients with AIDS", *Lancet* 343:577–578 (1994).
Luka et al., "Isolation of Human Herpesvirus–6 From Clinical Specimens Using Human Fibroblast Cultures", *J. Clinical Laboratory Analysis* 4:483–486 (1990).
Lusso et al., "Human Herpesvirus 6 in AIDS", *Immunology Today* 16:67–71 (1995).
Pel–Freez Brouchure (HHV6 Immediate Early Protein Antibodies), Published Jul. 17, 1995.
Salahuddin et al., "Isolation of a New Virus, HBLV, in Patients with Lymphoproliferative Disorders", *Science* 23:596–600 (1986).
Secchiero et al., "Detection of Human Herpesvirus 6 in Plasma of Children with Primary Infection and Immunosuppressed Patients by Polymerase Chain Reaction", *J. Infectious Diseases* 71:273–280 (1995).
Simmons et al., "Replication of Human Herpesvirus 6 in Epithelial Cells In Vitro", *J. Infectious Diseases* 166:202–206 (1992).
Takeda et al., "Prokaryotic Expression of an Immediate–Early Gene of Human Herpesviurs 6 and Analysis of its Viral Antigen Expression in Human Cells", *Virus Research* 41:193–200 (1996).
Yamanishi et al., "Identification of Human Herpesvirus–6 as a Causal Agent for Exanthem Subitum", *The Lancet* May, 1988:1066–1067.
Yamanishi et al., "Idiopathic Thrombocytopenic Purpura After Human Herpesvirus 6 Infection", *The Lancet* p. 830 (1994).
Carrigan et al., Abstracts of the General Meeting of the American Society for Microbiology 96(O):25 (1996).
Martin et al., *J. Virology* 65(10):5381–5390 (1991).

*Primary Examiner*—Phuong T. Bui
*Attorney, Agent, or Firm*—Quarles & Brady LLP

[57] ABSTRACT

An antibody raised against an epitope of a peptide having an amino acid sequence selected from a group consisting of Leu Asp Gly Tyr Pro Ser Asp Tyr Asp Pro Phe Val Glu Asn Ala Gln Ile Tyr (SEQ ID NO:1) and Leu Asp Gly Tyr Pro Ser Asp Tyr Asp Pro Phe Glu Glu Asn Ala Gln Ile Tyr (SEQ ID NO:2) is advantageously used in an indirect immunoassay to detect the presence of active Human Herpesvirus-6 in a patient sample.

1 Claim, No Drawings

ANTIBODY TO CARBOXY–TERMINUS OF HUMAN HERPESVIRUS 6 IMMEDIATE EARLY PROTEIN

CROSS-REFERENCE TO RELATED APPLICATIONS

This application is a divisional application of Ser. No. 08/683,060, filed Jul. 16, 1996 now U.S. Pat. No. 5,756,302.

FIELD OF THE INVENTION

The present invention relates to assays for detecting viruses and more particularly to the specific detection of Human Herpesvirus 6, and to an assay for distinguishing variant forms of the virus.

BACKGROUND OF THE INVENTION

Human Herpesvirus 6 ("HHV-6"), a beta herpesvirus first described by Salahuddin and colleagues in 1986, is present in a latent state in about ninety percent of the human population. During periods of active infection, however, the virus is associated with various clinical illnesses.

HHV-6 is genotypically and phenotypically subtyped into variant forms A and B ("HHV-6A" and "HHV-6B", respectively). HHV-6B is responsible for the majority of clinical illness associated with HHV-6 in humans. Much less is known about pathology of HHV-6A. HHV-6 is genetically distinct from the other herpesvirus, which include Herpes Simplex Virus-1, Herpes Simplex Virus-2, Cytomegalovirus, Epstein-Barr Virus and Varicella Zoster Virus.

HHV-6 is the clinical etiological agent of roseola infantum and exanthem subitum in children and is commonly associated with clinically significant bone marrow suppression in infants with primary HHV-6 infections. In adults, HHV-6 is causally associated with a wide spectrum of clinic illness, which can be fatal in at-risk immunocompromised or immunosuppressed populations. Notably, HHV-6 is prominent in patients having pneumonitis and encephalitis and in patients immunosuppressed following allogeneic bone marrow transplant (AlBMT) or solid organ transplant.

In AlBMT patients, HHV-6 associated bone marrow suppression (HBMS) correlates with direct viral infection of the bone marrow. Persistent infection by HHV-6 of bone marrow can cause chronic bone marrow suppression. In vitro experiments have both confirmed the bone marrow suppressive properties of HHV-6 and have shown that the suppression is mediated by cytokines or virus-produced soluble factors.

HHV-6 has also been suggested to be a co-factor in causation of HIV disease, and may be involved with febrile convulsions in children, multiple sclerosis, and chronic fatigue syndrome.

When HHV-6 is diagnosed promptly after infection, it can be treated effectively using available antiviral agents such as ganciclovir and foscarnet which suppress viral replication. Unfortunately, the art has been forced to rely upon one of three difficult, expensive and time consuming methods for diagnosing active HHV-6 infection.

The preferred available diagnostic method involves isolating the virus from cell culture after co-cultivating a patient sample with mitogen-stimulated umbilical cord lymphocytes for a period that can be as long as three weeks. This procedure is not routinely available in virology laboratories, and is too slow to be of practical use to clinicians.

Active HHV-6 infection can also be demonstrated using a polymerase chain reaction (PCR) protocol to detect HHV-6 viral DNA in an acellular specimen such as cerebro-spinal fluid or serum. This technique, too, is generally unavailable and expensive.

Finally, active HHV-6 infection is shown by positive immunohistochemical staining of a tissue biopsy or cytological preparation (e.g., BAL) using an antiserum or monoclonal antibody that reacts with late-appearing viral structural proteins. This third technique is highly specialized, is not routinely available in histology laboratories, and is less likely to detect early HHV-6 infections.

Since effective treatment depends upon early diagnosis of infection, an improved ability to facilitate early detection of HHV-6 is desired.

SUMMARY OF THE INVENTION

In a first aspect, the present invention is summarized in that various novel polyclonal and monoclonal antibody reagents are specific for the native major immediate early gene product of the HHV-6 virus. In addition to permitting rapid detection of an HHV-6 protein, certain of the novel reagents can distinguish A-variant from B-variant strains.

The antibody reagents are directed to a defined immunogenic peptide that comprises the carboxy-terminal amino acids of the HHV-6 immediate early protein. In A variant strains of HHV-6, the carboxy-terminal eighteen amino acids have the following sequence: Leu Asp Gly Tyr Pro Ser Asp Tyr Asp Pro Phe Val Glu Asn Ala Gln Ile Tyr (SEQ ID NO:1). In variant B strains, the corresponding carboxy-terminal amino acid sequence is Leu Asp Gly Tyr Pro Ser Asp Tyr Asp Pro Phe Glu Glu Asn Ala Gln Ile Tyr (SEQ ID NO:2). These two peptides specifically induce B-cell clones that produce antibodies specific for the HHV-6A and B variants, and for each individual variant. Such B-cell clones can be fused with immortal cell lines to form hybridomas that secrete immunospecific monoclonal antibodies.

The antibodies have little cross-reactivity with other cellular or viral antigens in infected cells because they specifically recognize a short, defined peptide.

In a second aspect, a rapid direct or indirect immunofluorescence assay for detecting active HHV-6 infection in a test sample utilizes the novel antibody reagents. Active HHV-6 infection can be detected indirectly by first associating or binding one of the antibody reagents to the immediate early protein in infected cells and then supplying a second antibody reagent for detecting the associated or bound antibody.

When the first antibody binds the protein and the second antibody binds to the first antibody, the infected cells can be visualized. If the antibody reagent itself includes a detectable portion, the assay can be a direct immunoassay. Antibodies directed against other determinants of the native immediate early protein that had been predicted to be immunogenic do not stain HHV-6-infected cells in the assay.

It is an object of the present invention to speed diagnosis of HHV-6 virus infection, so that diagnosis is accomplished more readily, in less time, and at lower cost, than is possible using existing techniques.

Another object of the present invention is to provide a reagent specific for a product of the major HHV-6 immediately early gene, so that infection can be diagnosed just hours or days after infection or reactivation.

It is yet another object of the present invention to provide a battery of reagents that can distinguish between A- and B-variant HHV-6 strains.

Other objects, advantages and features of the present invention will become apparent upon consideration of the accompanying Detailed Description of the Invention.

DETAILED DESCRIPTION OF THE INVENTION

To produce HHV-6-specific antibodies, the peptide comprising amino acids from the carboxy-terminal portion of the HHV-6 immediate early ("IE") protein is conjugated to a carrier which can be bovine serum albumin or, more preferably, the polylysine-based Multiple Antigen Peptide (MAP; Research Genetics, Huntsville, Ala.) product and is then injected into an animal host capable of generating an immune response to the peptide. Methods for injecting an immunogenic peptide into an animal host are well known.

The amino acid sequence of the peptide to inject depends upon whether an antibody directed to an A-variant or B-variant strain is desired. In A-variant strains, the peptide sequence is Leu Asp Gly Tyr Pro Ser Asp Tyr Asp Pro Phe Val Glu Asn Ala Gln Ile Tyr (SEQ ID NO:1). In B-variant strains, the amino acid sequence in the antigenic peptide is Leu Asp Gly Tyr Pro Ser Asp Tyr Asp Pro Phe Glu Glu Asn Ala Gln Ile Tyr (SEQ ID NO:2). These two 18-amino acid long sequences differ only at the twelfth amino acid position. Thus, some antibodies raised against each peptide after injection into a host animal are directed to common epitopes of the peptide. These antibodies function well to indicate HHV-6 infection, but cannot distinguish between variants. On the other hand, certain antibodies directed to the variant-specific epitopes of the two peptides are useful reagents for specifically diagnosing infection with an A-variant or a B-variant strain.

Moreover, the peptide can be somewhat longer than the eighteen bases shown herein to encode the epitope(s). One of ordinary skill will appreciate that the desired epitope(s) will remain if additional amino acids (say up to about 50 amino acids) are included in the peptide. Such extra amino acids can correspond structurally to the IE protein or can be non-immunogenic amino acid chains. However, it is also understood that by lengthening the amino acid, other antibodies of unknown specificity can be induced, hindering production of the desired reagents. It will further be understood that suitable reagents (that are more or less reactive with the IE protein) may be produced even if one or more amino acids from one end or the other of the exemplified peptide are absent from the immunogenic peptide.

The sequence of the gene that encodes the IE protein has been determined, and predicted amino acid sequences for the protein in various variant strains are known (Chou, S. and G. Marqusek, "Analysis of Interstrain Variation in a Putative Immediate-Early Region of Human Herpesvirus 6 DNA and Definition of Variant-Specific Sequences," *Virology* 198:370–376 (1994), incorporated herein by reference). The carboxyl end of the IE proteins known to date is conserved, except for this single amino acid change. The invention could be applied with equal force, however, to other peptides from the carboxyl end of the IE gene that may be uncovered in the future, since antibodies directed against sequences containing minor variations would likely still have diagnostic use for HHV-6, and could retain an ability to distinguish A-variants from B-variants (or other variants as yet unknown). These variant peptides could include peptides having amino acid changes at positions other than position 12, where the changed amino acids are structurally similar to the amino acids of the indicated peptides and where the overall tertiary structure of the peptide is not appreciably altered and where HHV-6 specific epitopes remain. Such variations, which shall be considered to correspond to the exemplified peptides, would include, for example, peptides having side chain variants of the exemplified amino acids.

The above-noted sequences were unique among nine sequences predicted to include potential antigenic determinants by computer analysis (using the Peptide Structure Program commercially available from Genetics Computer Group, Madison, Wis.). Of the selected sequences, only the carboxy-terminal peptide (including both variants) elicited a specific response to the native IE protein. Moreover, Takeda, et al., "Prokaryotic expression of an immediate-early gene of human herpesvirus 6 and analysis of its viral antigen expression in human cells," *Virus Research* 41:193–200 (1996) have reported that a fusion protein comprising the carboxyl end of the IE protein did not react with human anti-HHV-6 serum. The inventors are not aware that anti-HHV-6 immunogenicity has previously been observed in the carboxyl portion of the IE protein. Although Takeda, et al. tested a different strain of HHV-6, the IE protein was demonstrated to have the identical carboxy-terminal sequence to the A-variant strain used by the present inventors.

It may be possible to prepare the injected peptide by cleaving native IE protein isolated from infected cells. However, since the protein is quite rare in infected cells, the protein itself has not heretofore been purified, so this method is not preferred. More practically, the amino acid sequence can be chemically synthesized or isolated from a host cell containing a recombinant DNA vector engineered to express the desired peptide as part of a fusion protein. Either of these methods is available to one having ordinary skill in the art.

The host in which the immune response is induced can be selected by one having ordinary skill in the art. A typical system involves injecting the selected conjugated peptide into rabbits to produce an IgG response. Serum obtained from such immunized rabbits contains polyclonal antibodies having specificity against the immunogen. Alternatively, the selected conjugated peptide can be injected into suitably primed mice to induce antibody-producing B-cells which can be fused with an immortalized cell line using conventional techniques, to prepare hybridomas that secrete monoclonal antibodies diagnostic for one variant strain type or monoclonal antibodies that recognize more than one HHV-6 variant type.

The specificity of the polyclonal or monoclonal antibodies can be assessed by screening the antibodies in an immunofluorescence assay using cells known to be infected with HHV-6. In particular, the antibodies obtained can be incubated with HHV-6A-infected HSB-2 cells or HHV-6B-infected normal PHA-stimulated peripheral blood mononuclear cells ("PBMC"). Antibodies bound or associated to the infected cells, which are typically IgG antibodies, can themselves be visualized in the indirect assay using a fluorescent-tagged second antibody or an enzyme-conjugated second antibody, or any other known method for detecting a class of antibodies. The second antibody, directed against IgG from the host animal species, can be raised in a different species. The enzyme-conjugated second antibody can employ a horseradish peroxidase/substrate system. The fluorescent-tagged second antibody can be fluorescein isothiocyanate (FITC)-tagged. A preferred system for detecting anti-HHV-6 IgG antibodies produced in rabbits uses a fluorescein isothiocyanate (FITC)-conjugated goat anti-rabbit IgG in Evan's Blue counterstain. The amount of antiserum and visualizing antibody are adjusted to maximize the staining contrast between the infected cell nucleus and the cellular background.

A direct fluorescent tagging of the primary antibodies specific for HHV-6 is also possible. This procedure would eliminate the need for the fluorescent-tagged second antibody. The antibodies could also be used in an immunoassay of cellular extracts or lysates, where after infection, the cell membranes of the host cells are weakened or removed and the immediate early protein is assayed after release from the cells. It is intended that the concept of "fixing" the cells is in preparation for cellular assays (as in the Example) or assays of lysates or extracts.

The HHV-6 IE gene product revealed by the immunofluorescence assay is observed even in cells showing advanced viral cytopathic effects, which indicates that the antigenic target of the antiserum is expressed throughout the replicative cycle of the virus. To ensure that the antibodies indeed detect the IE protein, infected cells can be treated sequentially with cycloheximide and actinomycin D immediately after infection. Such treatments block further viral protein synthesis and RNA synthesis, respectively, ensuring that antibodies only bind to protein produced immediately after infection.

The following indirect immunoassay which employs the antibody or antibodies described above, is advantageously employed to diagnose HHV-6 infection in patients. The method for preparing the specific antibodies for use in the diagnostic assay is not critical to the present invention. It will be understood by those having ordinary skill that the variant-A or variant-B status of an HHV-6 strain can be determined in a pair of assays using a pair of antibodies where each antibody is specific to one of the variants, or by using a pair of antibodies where one antibody is specific to one variant and the other antibody recognizes both variants. A preferred form of this assay is a rapid shell vial spin assay described in the Example. The shell vial spin assay is similar to that described by Gleaves, C. A. et al., *J. Clin. Microbiol.* 19:917–919 (1984) and by Gleaves, C. A. et al., *J. Clin. Microbiol.* 21:217–221 (1985), both of which are incorporated herein by reference. ViroMed Laboratories, Inc. (Minneapolis, Minn.) also makes information on such assays available to its customers in a document entitled Diagnostic Techniques Utilizing Cell Cultures (pages 38–39), which is also incorporated herein by reference.

Various patient sample material can be tested for HHV-6 in the assay. In each case, it is desired that the tested material be homogeneous. PMBC are a preferred test material. In addition, bone marrow aspirate, tissue biopsies (notably lung biopsies) are also known to contain HHV-6. It is specifically envisioned that an direct or indirect immunoassay of the types described herein can be used to diagnose HHV-6 infection in paraffin-embedded sections using standard techniques for introducing antibody reagents into paraffin samples. The antibody reagents may also be applied in assays to test non-cellular material, including but not limited to cerebrospinal fluid, plasma, serum and urine, or to solid organ tissue samples such as kidney, liver and lymph node samples.

Cellular or non-cellular patient sample materials to be tested for HHV-6 are added to a host cell line permissive or semi-permissive for HHV-6 IE gene expression. The host cells are preferably grown as a confluent monolayer on a glass cover slip, which simplifies subsequent treatment with the antibody reagents. Various cells that can be used as the host cell in the assay. MRC-5 cells, a diploid human lung cell line obtained from normal lung tissue of a 14 week old male fetus (Jacobs, J. P. et al., *Nature* 227:168–170 (1970) are semi-permissive for HHV-6, in that viral proteins are produced but infectious virus is not assembled. MRC-5 cells are suitable host cells and are commercially available from various sources such as ViroMed Laboratories, Inc., Bartells, a division of Intracel (Issaquah, Wash.), and Bio-Whittaker (Walkersville, Md.). ViroMed Laboratories, in particular, sells shell vials containing a cover slip with a monolayer of MRC-5 cells on the cover slip. These commercial shell vials are most preferred for use in the assay described herein.

HHV-6 has also been shown to propagate in vitro in human adult and umbilical cord lymphocytes, human T-cell lines, thymocytes and epithelial cells. The host cells need not be of human origin, but should be animal cells. In particular, NBL-7 mink lung cells (ATCC CCL64) are known to be a suitable host for HHV-6. Such cells and, presumably, other blood and epithelial cells can also be suitable hosts in an assay that may be adaptable so as not to require a monolayer of cells.

The cells are brought into close contact with one another, preferably by centrifugation which is thought either to provide a high level of direct cell-to-cell contact or to stretch the host cell membranes sufficiently to permit viral infection. Centrifugation for 45 minutes at 800× g (25° C.) is adequate. The cells are then incubated under physiological conditions (at or near 37° C., about 5% $CO_2$ atmosphere) until the fibroblastoid cells become infected and begin to produce the IE protein. An incubation period of between 48 and 72 hours is adequate.

After incubation, the host cells are washed in a buffered solution, fixed in acetone, and allowed to air dry. To reduce background, normal goat serum diluted in a buffered solution is added and incubated for a short period of time at physiological temperature in a humidified environment. The goat serum is removed and is replaced by the antibody directed to the desired peptide. Again the antibody is incubated with the host cells for a short period of time at physiological temperature in a humidified environment.

Non-specific antibody is removed by washing the cells several times in a buffered solution. The second, detecting antibody (generally an appropriate FITC-conjugated anti-IgG antibody) is added in diluted normal goat serum containing the counterstain and is incubated for a short time at physiological temperature in a humidified environment. Again, unbound antibody is removed by washing the cells several times in buffered solution.

The cells can then be scanned to reveal the presence of HHV-6 IE protein. For the procedure described above, fluorescent microscopy at 200X of cells on cover slips is suitable. Higher magnification can be used to differentiate between specific and non-specific staining in questionable samples. A sample is considered positive if two or more fibroblasts containing speckled or diffuse nuclear staining are observed and nuclear staining is absent on negative control cover slips.

As noted above, other detection schemes are possible. If an enzyme-linked antibody is used as the detecting antibody, the cells can be bathed in a suitable substrate that permits visualization of stained cells using light microscopy or other suitable visualization means.

EXAMPLE

Selecting potential antigenic determinants The predicted amino acid sequence of the HHV-6 IE protein was analyzed using the Peptide Structure Program available from the Genetics Computer Group, Madison, Wis. The software identifies regions of a protein having a high antigenic index, taking into account the secondary structure of the protein, the hydrophilicity, the surface probability, the flexibility, and the Chou-Fasman and Garnier-Osquthorpe-Robson factors. Nine amino acid sequences having a high antigenic index were identified in the IE protein. The amino acid sequences were synthesized, conjugated to BSA, and injected into rabbits using standard immunization protocols. Only antisera prepared against the carboxyterminal peptide having amino acid sequence Leu Asp Gly Tyr Pro Ser Asp Tyr Asp Pro Phe Glu Glu Asn Ala Gln Ile Tyr (SEQ ID NO:2) bound specifically to the nuclei of HHV-6 infected cells. The staining was confirmed to be specific for the IE antigen of HHV-6 by sequential treatment of infected cells with cycloheximide and actinomycin D immediately after infection. The polyclonal antibody was subsequently shown to have specificity for both variant forms of HHV-6.

Using this procedure and a comparable procedure in mice for producing monoclonal antibodies, both of the selected peptides were employed in separate trials to produce one monoclonal antibody that recognized both A- and B-variants of HHV-6, two monoclonal antibodies directed against HHV-6B, and one monoclonal antibody directed against HHV-6A.

The antibodies identify a protein of about 100 kilodaltons on western blots of virus infected cell lysates. The stained protein is expressed in infected cells sequentially treated with cycloheximide and actinomycin D.

Diagnosis of HHV-6 infection

PBMC were purified from sodium heparin anticoagulated blood by Ficoll-Hypaque gradient. The PBMC were washed once with Hank's balanced salt solution (HBSS) and were then re-suspended in 1.0 ml of RPMI-1640 supplemented with 10% fetal calf serum, 20 mM HEPES and 2 µg/ml polybrene. Each sample of mononuclear cells was divided into four samples of 0.25 ml each. Each sample was added to a shell vial containing a confluent monolayer of MRC-5 human fibroblasts (ViroMed Laboratories, Inc. (Minneapolis, Minn.)) on a glass cover slip. A positive control was established by adding infected cells or cell lysates from cells known to be HHV-6 positive. An uninfected shell vial served as a negative control.

The shell vials were then centrifuged for forty-five minutes at 800× g at 25° C. Following centrifugation, the vials were incubated at 37° C. in a humidified 5% $CO_2$ atmosphere for 48–72 hours.

After incubation, the cell cover slip monolayers were washed four times in HBSS and fixed in acetone (at −20° C.) for ten minutes. The fixed cover slips were allowed to air dry.

Next, 0.3 ml of 2% normal goat serum in phosphate buffered saline (NGS/PBS) was added to each vial and the vials were incubated at 37° C. for 30 minutes in a humidified incubator. The NGS/PBS was decanted and replaced with the appropriate dilution of rabbit anti-HHV-6 antibody in NGS/PBS. The cover slips were incubated at 37° C. for 30 minutes in a humidified incubator. The primary antibody was then decanted and the cover slips were washed four times for five minutes each with HBSS. Next, the appropriate dilution of FITC-conjugated second antibody in NGS/PBS containing 0.01% Evan's Blue counterstain was added and the cover slips were again incubated at 37° C. for 30 minutes in a humidified incubator. The secondary antibody-FITC conjugate was decanted and the cover slips were washed four times for five minutes each with HBSS. The cover slips were then mounted (cells down) on microscope slides with buffered glycerol and were scanned with fluorescent microscopy at 200×. A cell was regarded as positive if two or more speckled or diffuse nuclear stained fibroblasts were detected on the test cover slip and if nuclear staining was absent from the negative control cover slips.

Comparative method

To compare the effectiveness of the present method to existing protocols for diagnosing HHV-6 infection, the following virus isolation protocol was performed exactly as previously described by Drobyski, W. R. et al., *J. Infect. Dis.* 167:735 (1993) and by Carrigan, D. R. and K. K. Knox, *Blood* 84:3307 (1994), both incorporated herein by reference. PBMC and low-density bone marrow cells were isolated by ficoll-hypaque density gradient centrifugation. Tissue biopsies were homogenized and clarified by centrifugation. The final volume of each specimen was adjusted to 1 ml of RPMI-1640 medium with 10% fetal calf serum and 2 µg/ml of polybrene. One-half ml of each specimen was then mixed with phytohemagglutinin (PHA)-stimulated PBMC from HHV-6 seronegative normal donors or PHA-stimulated umbilical cord mononuclear cells. The cultures were then observed every second day for the appearance of HHV-6 cytopathic effects. Indirect immunofluorescent staining with an HHV-6A specific monoclonal antibody (2D6) and an HHV-6B specific monoclonal antibody (C3108-103) were performed to confirm that the viruses isolated were HHV-6 and to determine the virus variant identity of each isolate. Uninfected control cells were included in every virus isolation procedure. HHV-6 was never detected in any uninfected control sample.

Comparative results

Forty-three specimens from 30 immunocompromised patients were simultaneously subjected to both the rapid shell vial assay and HHV-6 isolation using mitogen-stimulated PBMC. Each sample was obtained from a patient with clinical disease that was potentially attributable to active HHV-6 infection (i.e., pneumonitis, bone marrow suppression, or encephalitis). The tissue samples were both lung biopsies. All virus isolates were confirmed to be HHV-6 variant B by indirect immunofluorescence with the specific monoclonal antibodies.

The patient status, the samples analyzed, and the virus isolation results are summarized in Table 1.

TABLE 1

Summary of Patients and HHV-6 Isolation Results

|  |  | Type of Sample | | |
| --- | --- | --- | --- | --- |
| Patient Group | Number of Patients | Blood | Bone Marrow | Tissue Biopsy |
| Chemotherapy Recipients | 2 | 0/0[1] | 1/2 | 0/0 |
| Organ Transplant Recipients | 4 | 1/6 | 0/0 | 0/0 |
| Bone Marrow Transplant Recipients | 24 | 1/7 | 4/23 | 0/2 |
| Total | 30 | 2/13 | 5/25 | 0/2 |

[1]HHV6 Isolation Positive/Total Number of Samples

The rapid shell vial assay and virus isolation methods are compared in Table 2, a 2×2 contingency table. Every sample that was positive for HHV-6 by virus isolation was also positive by the rapid shell vial assay, except for one blood sample from a liver transplant recipient.

TABLE 2

Two by Two Contingency Table Showing Correlation Between HHV-6 Isolation and the Rapid Shell Vial Assay[1]

|  |  | Rapid Shell Vial Assay | |
| --- | --- | --- | --- |
| Method |  | + | − |
| Virus Isolation | + | 6 | 1 |
|  | − | 0 | 33 |

Specificity = 100%
Sensitivity = 86%
Statistics
The data was analyzed using the Fisher's Exact Test and proved significant at the p > 0.0001 level.
[1]Three specimens were excluded from this analysis; the virus isolation attempt was aborted due to toxicity of the specimen in cell culture.

The data presented herein demonstrate that the described assay is both sensitive and highly specific for detecting active HHV-6 infections in a variety of patient specimens. Its simplicity and rapid turnaround time also make it a useful and practical addition to microbiology and virology clinical laboratories.

The present invention is not intended to be limited by the preceding example, but rather to encompass all such modifications and variations as come within the scope of the appended claims.

What is claimed is:

1. An isolated antibody raised against an epitope of an 18 amino acid long carboxy-terminal peptide of HHV-6 major immediate-early protein, the peptide having an amino acid sequence selected from the group consisting of SEQ ID NO:1 and SEQ ID NO:2.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: peptide (vi) ORIGINAL SOURCE:
       (A) ORGANISM: Human Herpesvirus-6 (variant A)

(xi) SEQUENCE DESCRIPTION: SEQ ID NO:1:

Leu Asp Gly Tyr Pro Ser Asp Tyr Asp Pro Phe Val Glu Asn Ala Gln
   1               5                   10                  15

Ile Tyr (2) INFORMATION FOR SEQ ID NO:2:

-continued

```
    (i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Human Herpesvirus-6 (Variant B)

(xi) SEQUENCE DESCRIPTION: SEQ ID NO:2:

Leu Asp Gly Tyr Pro Ser Asp Tyr Asp Pro Phe Glu Glu Asn Ala Gln
   1               5                   10                  15

Ile Tyr
```